US010772719B2

(12) United States Patent
Eaton et al.

(10) Patent No.: US 10,772,719 B2
(45) Date of Patent: Sep. 15, 2020

(54) METHOD OF MAKING A CONTOURED INTERNAL LIMB FOR A PROSTHESIS AND PROSTHESIS WITH A CONTOURED INTERNAL LIMB

(71) Applicant: Cook Medical Technologies LLC, Bloomington, IN (US)

(72) Inventors: Elizabeth A. Eaton, Bloomington, IN (US); Allen E. Hacker, Bloomington, IN (US); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 287 days.

(21) Appl. No.: 15/886,035

(22) Filed: Feb. 1, 2018

(65) Prior Publication Data
US 2018/0228592 A1    Aug. 16, 2018

Related U.S. Application Data

(60) Provisional application No. 62/458,771, filed on Feb. 14, 2017.

(51) Int. Cl.
*A61F 2/07* (2013.01)
*A61F 2/82* (2013.01)
(Continued)

(52) U.S. Cl.
CPC ............ *A61F 2/07* (2013.01); *A61F 2/89* (2013.01); *A61F 2002/061* (2013.01);
(Continued)

(58) Field of Classification Search
CPC .............. A61F 2/07; A61F 2002/072; A61F 2002/075; A61F 2002/077
See application file for complete search history.

(56) References Cited

U.S. PATENT DOCUMENTS 5,156,619 A * 10/1992 Ehrenfeld ............... A61F 2/06
                                                              623/1.31
5,643,340 A *  7/1997 Nunokawa ............. A61F 2/06
                                                              623/1.49
(Continued)

FOREIGN PATENT DOCUMENTS

WO    WO 2002/22055 A2    3/2002
WO    WO 2013/071222 A1   5/2013
(Continued)

OTHER PUBLICATIONS

European Extended Search Report and Written Opinion for European Patent Application No. 18275018.2 dated May 29, 2018 (7 pages).
(Continued)

*Primary Examiner* — Jacob J Cigna
(74) *Attorney, Agent, or Firm* — Brinks Gilson & Lione

(57) ABSTRACT

A method of making a contoured internal limb including providing a flattened tubular segment of graft material, and a prosthesis including the contoured internal limb. The tubular segment includes a left lateral edge, a right lateral edge, a first length extending from the left lateral edge to the right lateral edge, and a second length extending from a proximal end to a distal end of the tubular segment. The method also includes contouring a proximal portion, a middle portion, and a distal portion of the contoured internal limb from the tubular segment. The method also includes closing a right lateral edge of the proximal portion and a right lateral edge of a first section of the middle portion. The method further includes removing the proximal, middle and distal portions of the contoured internal limb from the tubular segment and maintaining a second section of the middle portion as circumferentially continuous.

16 Claims, 12 Drawing Sheets

(51) Int. Cl.
*A61F 2/06* (2013.01)
*A61F 2/89* (2013.01)

(52) U.S. Cl.
CPC ... *A61F 2002/067* (2013.01); *A61F 2002/826* (2013.01); *A61F 2220/0075* (2013.01); *A61F 2230/0019* (2013.01); *A61F 2240/001* (2013.01)

(56) References Cited

U.S. PATENT DOCUMENTS

| | | | | |
|---|---|---|---|---|
| 5,755,734 | A * | 5/1998 | Richter | A61F 2/07 606/194 |
| 5,755,735 | A * | 5/1998 | Richter | A61F 2/07 606/194 |
| 5,906,640 | A * | 5/1999 | Penn | A61F 2/91 623/1.15 |
| 5,968,089 | A * | 10/1999 | Krajicek | A61B 17/11 623/1.15 |
| 6,251,133 | B1 * | 6/2001 | Richter | A61F 2/07 623/1.16 |
| 6,395,018 | B1 | 5/2002 | Castaneda | |
| 6,436,134 | B2 * | 8/2002 | Richter | A61F 2/07 623/1.15 |
| 6,454,796 | B1 * | 9/2002 | Barkman | A61F 2/07 623/1.35 |
| 6,524,335 | B1 | 2/2003 | Hartley et al. | |
| 6,645,242 | B1 * | 11/2003 | Quinn | A61F 2/07 623/1.13 |
| 6,743,243 | B1 * | 6/2004 | Roy | A61B 17/11 606/153 |
| 6,811,566 | B1 * | 11/2004 | Penn | A61F 2/91 623/1.15 |
| 6,949,121 | B1 | 9/2005 | Laguna | |
| 7,014,653 | B2 | 3/2006 | Ouriel et al. | |
| 7,022,134 | B1 * | 4/2006 | Quijano | A61F 2/2412 623/1.24 |
| 7,029,496 | B2 * | 4/2006 | Rakos | A61F 2/07 623/1.35 |
| 7,407,509 | B2 | 8/2008 | Greenberg et al. | |
| 7,955,374 | B2 | 6/2011 | Erickson et al. | |
| 7,963,960 | B2 | 6/2011 | Bruszewski et al. | |
| 8,100,960 | B2 | 1/2012 | Bruszewski | |
| 8,118,861 | B2 * | 2/2012 | Hegg | A61F 2/856 623/1.16 |
| 8,241,349 | B2 | 8/2012 | Davidson et al. | |
| 8,556,961 | B2 * | 10/2013 | Quinn | A61F 2/07 623/1.35 |
| 8,574,288 | B2 * | 11/2013 | Hartley | A61F 2/07 623/1.16 |
| 8,728,148 | B2 * | 5/2014 | Roeder | A61F 2/07 623/1.11 |
| 8,864,819 | B2 * | 10/2014 | Hartley | A61F 2/07 623/1.13 |
| 8,915,956 | B2 | 12/2014 | Schaeffer et al. | |
| 8,945,205 | B2 * | 2/2015 | Greenberg | A61F 2/07 623/1.35 |
| 9,005,268 | B2 * | 4/2015 | Hartley | A61F 2/07 623/1.11 |
| 9,149,355 | B2 * | 10/2015 | Hartley | A61F 2/844 |
| 9,649,188 | B2 * | 5/2017 | Hartley | A61F 2/07 |
| 9,668,892 | B2 * | 6/2017 | Shalev | A61F 2/856 |
| 10,524,893 | B2 * | 1/2020 | Parodi | A61F 2/89 |
| 10,537,419 | B2 * | 1/2020 | Kratzberg | A61F 2/07 |
| 2003/0088306 | A1 * | 5/2003 | Rakos | A61F 2/07 623/1.13 |
| 2003/0199967 | A1 * | 10/2003 | Hartley | A61F 2/07 623/1.13 |
| 2004/0186560 | A1 * | 9/2004 | Alt | A61L 31/088 623/1.35 |
| 2004/0230287 | A1 * | 11/2004 | Hartley | A61F 2/954 623/1.12 |
| 2005/0059923 | A1 * | 3/2005 | Gamboa | A61F 2/07 604/9 |
| 2005/0131517 | A1 * | 6/2005 | Hartley | A61F 2/07 623/1.13 |
| 2005/0234542 | A1 * | 10/2005 | Melsheimer | A61F 2/07 623/1.35 |
| 2006/0030911 | A1 * | 2/2006 | Letort | A61B 18/1492 607/101 |
| 2006/0095118 | A1 | 5/2006 | Hartley | |
| 2007/0219621 | A1 * | 9/2007 | Hartley | A61F 2/07 623/1.13 |
| 2008/0300602 | A1 * | 12/2008 | Schmitt | A61B 17/8816 606/93 |
| 2009/0043377 | A1 | 2/2009 | Greenberg et al. | |
| 2009/0125097 | A1 | 5/2009 | Bruszewski et al. | |
| 2009/0228020 | A1 | 9/2009 | Wallace et al. | |
| 2009/0259290 | A1 | 10/2009 | Bruszewski et al. | |
| 2009/0264988 | A1 | 10/2009 | Mafi et al. | |
| 2010/0268327 | A1 * | 10/2010 | Bruszewski | A61F 2/07 623/1.18 |
| 2012/0041544 | A1 | 2/2012 | Wolf | |
| 2012/0046657 | A1 | 2/2012 | Biadillah et al. | |
| 2012/0197382 | A1 * | 8/2012 | Roeder | A61F 2/07 623/1.13 |
| 2012/0221096 | A1 * | 8/2012 | Roeder | A61F 2/07 623/1.13 |
| 2012/0239132 | A1 | 9/2012 | Naor et al. | |
| 2012/0296414 | A1 * | 11/2012 | Hartley | A61F 2/07 623/1.13 |
| 2013/0289702 | A1 | 10/2013 | Coghlan et al. | |
| 2013/0296998 | A1 | 11/2013 | Leotta et al. | |
| 2015/0119975 | A1 | 4/2015 | Mastracci | |
| 2016/0106564 | A1 | 4/2016 | Roeder et al. | |
| 2018/0116783 | A1 * | 5/2018 | Kratzberg | A61F 2/07 |

FOREIGN PATENT DOCUMENTS

| | | |
|---|---|---|
| WO | WO 2015/040413 A2 | 3/2015 |
| WO | WO 2015/061669 A1 | 4/2015 |
| WO | WO 2015/063780 A2 | 5/2015 |

OTHER PUBLICATIONS

Saari, P. et al., "*Fenestration of Aortic Stent Grafts-in Vitro Tests Using Various Device Combinations,*"Journal of Vascular and Interventional Radiology, vol. 22, Issue 1, (2011), pp. 89-94—Abstract Only—pp. 1-2.

Stephen, E. et al., "*A Novel Cautery Instrument for On-Site Fenestration of Aortic Stent-Grafts: A Feasibility Study of 18 Patients,*"Journal of Endovascular Therapy, 20, (2013) pp. 638-646.

\* cited by examiner

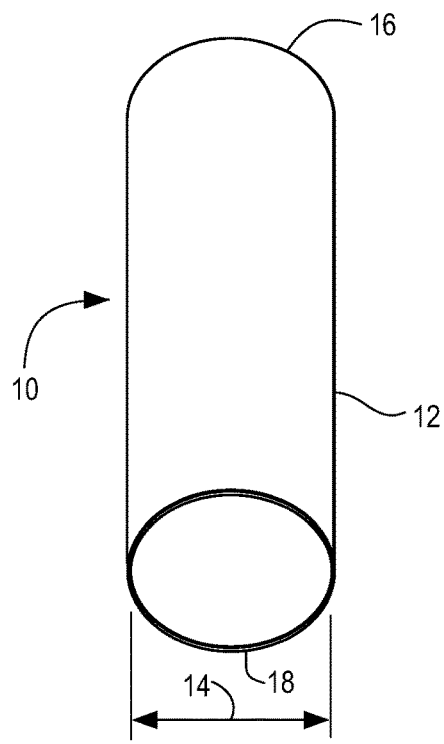
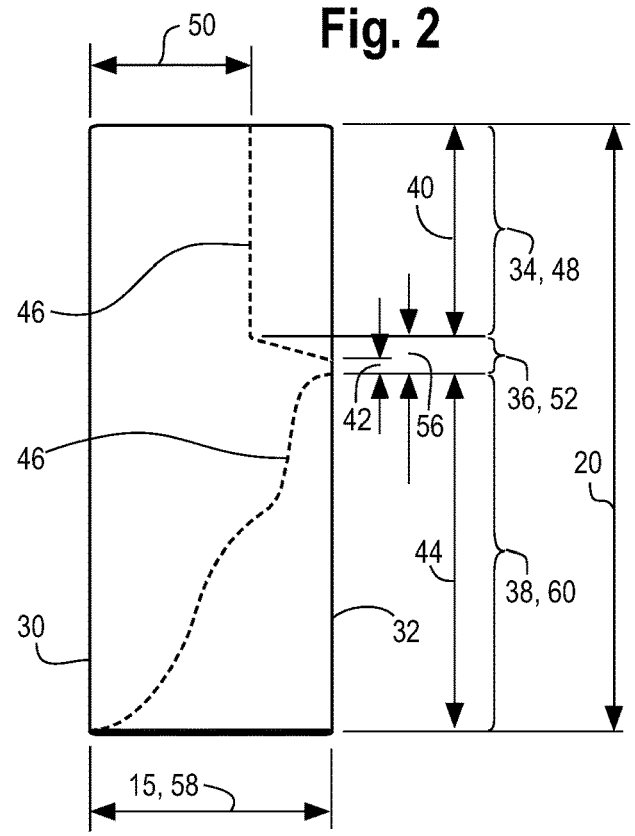
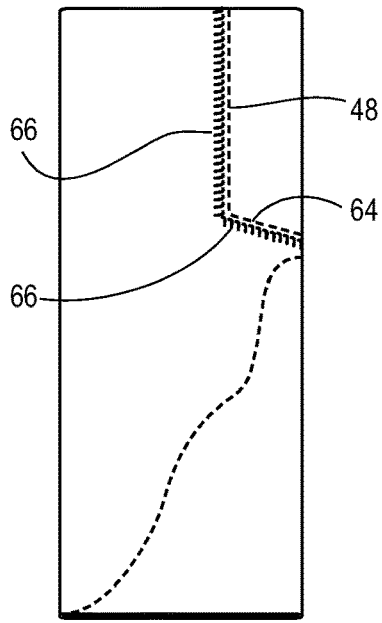
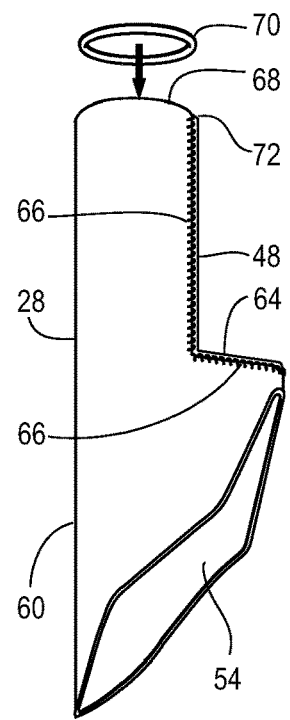
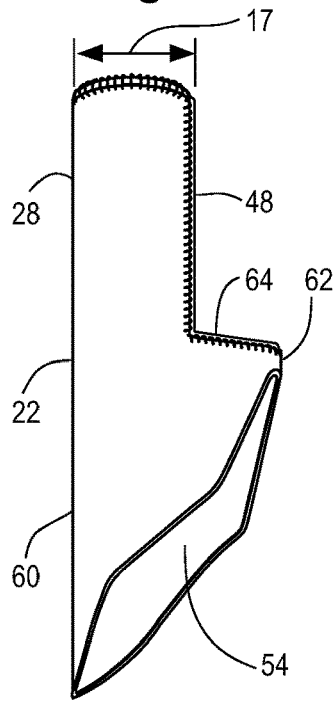

Fig. 10
Fig. 11
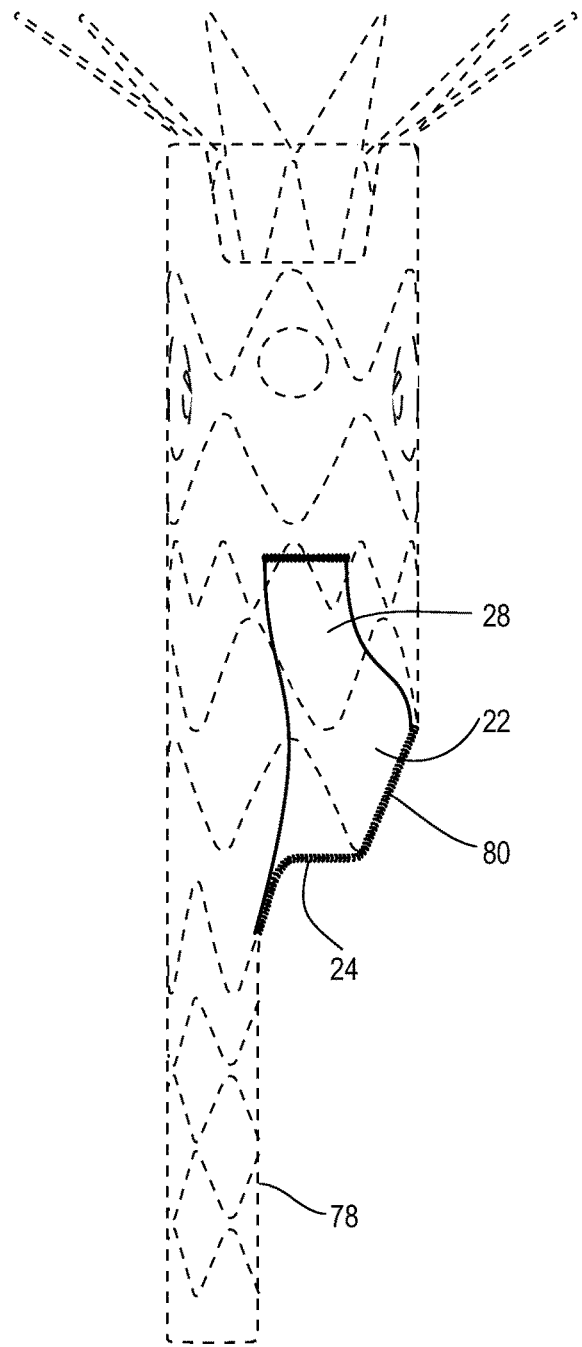
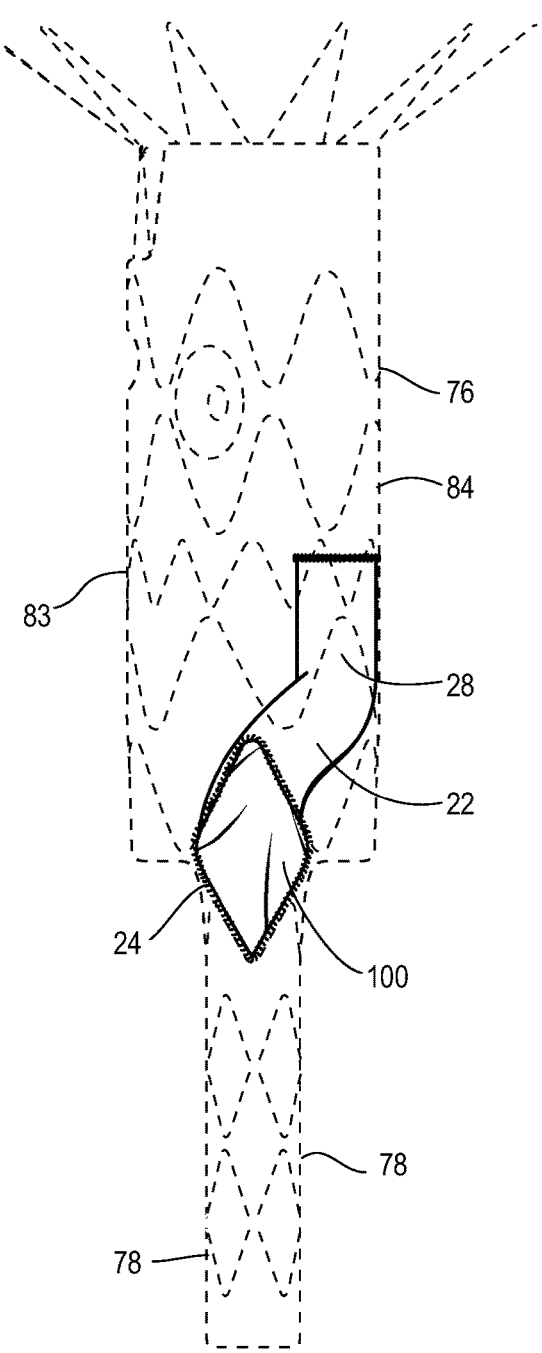

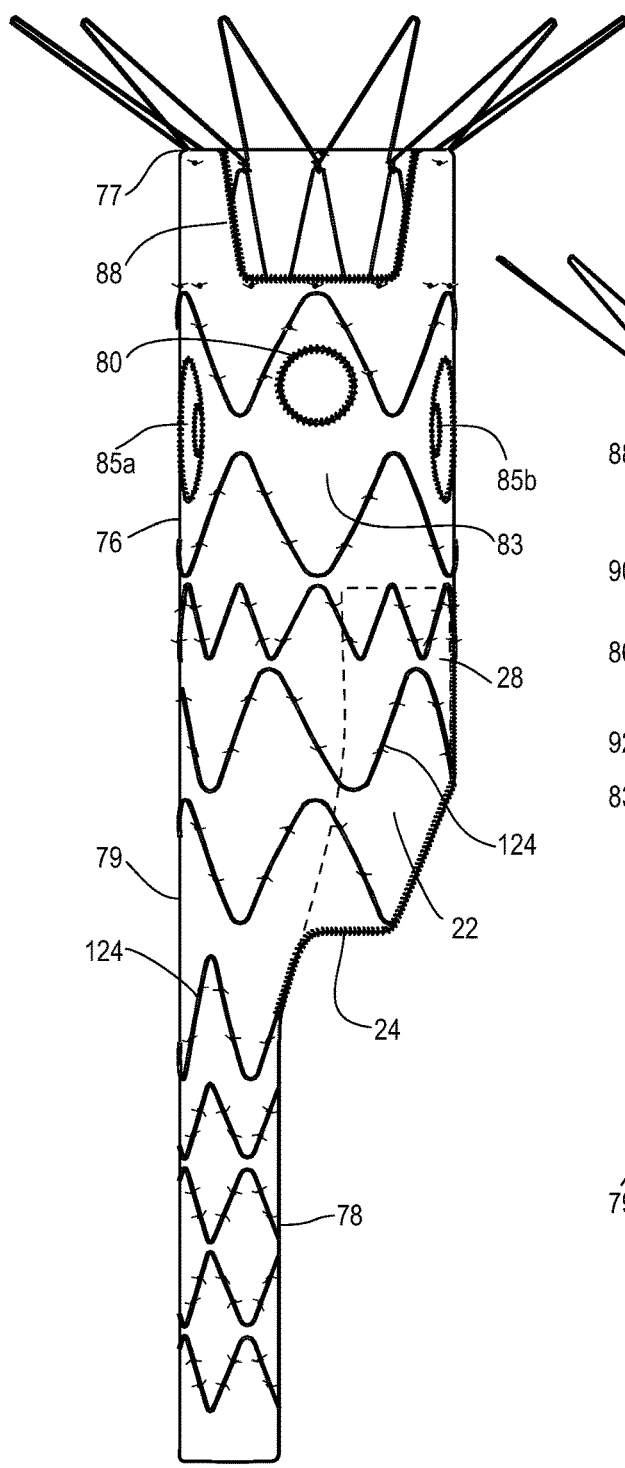
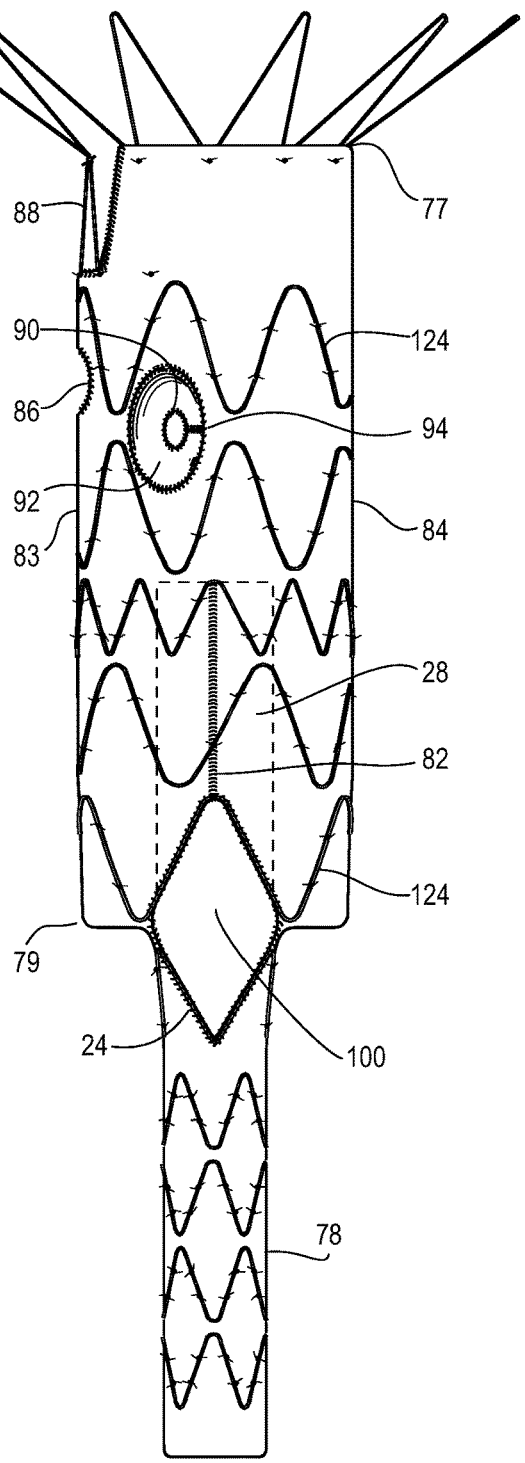

METHOD OF MAKING A CONTOURED INTERNAL LIMB FOR A PROSTHESIS AND PROSTHESIS WITH A CONTOURED INTERNAL LIMB

RELATED APPLICATIONS

The present patent document claims priority to and the benefit of the filing date under 35 U.S.C. § 119(e) to U.S. Provisional Patent Application Ser. No. 62/458,771, which was filed on Feb. 14, 2017, and is hereby incorporated by reference in its entirety.

BACKGROUND

1. Technical Field

The present invention relates to methods of making a contoured internal limb for a prosthesis, such as for abdominal aortic stent grafts, and prostheses including a contoured internal limb.

2. Background Information

Endovascular aortic aneurysm repair is practiced by a wide range of physicians across varying specialties. An aortic aneurysm is an enlargement of the aorta of a patient caused by weakening in the wall of the aorta. If an aortic aneurysm is untreated, it may rupture and cause serious health complications.

The surgical procedure for endovascular aortic aneurysm repair involves the placement of a stent graft within the aorta of a patient to seal off the aneurysm from blood flow to prevent the aneurysm from expanding. Physicians often use the procedure to treat abdominal aortic aneurysms (AAA) and also to treat thoracic aortic aneurysms (TAA) and aneurysms in other locations of the patient. One type of abdominal aortic aneurysm is an infra-renal abdominal aortic aneurysm, which is located in the abdominal aorta below the renal arteries.

As demographics continue to expand and graft recipients live longer, there is an increase in the prevalence and complexity of repair cases. The patient's anatomy may change over time and lead to a size mismatch of the original stent graft within the patient's anatomy or may result in movement of the stent graft within the patient's anatomy. The disease may also progress beyond the previously repaired area, which may result in endoleak at the stent graft seal zone or movement (migration) of the stent graft within the patient's anatomy. Additionally and/or alternatively, the original stent graft may have been implanted in suboptimal anatomy or the design or construction of the stent graft proves insufficient over time. These instances also may result in leaking of the stent graft, movement of the stent graft within the patient's anatomy, or other complications.

In addition, as the patient ages, other factors may also dictate treatment of the aortic aneurysm, including the frequency and severity of a patient's comorbidities and an increase in the patient's general surgical risk. These factors may rule the patients out as candidates for explant of the original stent graft during open repair.

To re-intervene endovascularly, the physician contends with not only maneuvering through the patient's anatomy, that potentially has grown more challenging or hostile in the interim, but also the body, legs, and limbs of the original stent graft. To reline the original stent graft, the physician must identify a landing zone for a new stent graft proximal to the original stent graft. This can mean new or further involvement of some of the visceral arteries, such as the renal arteries, the superior mesenteric artery, and the celiac artery. In most cases, the ostia of these vessels must be maintained: this frequently involves stenting with a covered stent through fenestrations in the new stent graft or apposing a scallop fenestration in the graft to the aortic wall at the level of the ostium. Another factor is the design of the original stent graft: the distance between the renal arteries and the proximal edge of the original stent graft affects whether the visceral arteries will be involved: and the distance between the proximal edge of the original stent graft and the bifurcation of the original stent graft dictates what kind of device will fit inside the existing environment. Some devices have a graft bifurcation located much farther proximally from the native aortic bifurcation than others, which truncates the acceptable body length of any device used in a reintervention. These factors create a highly complex procedure.

BRIEF SUMMARY

This invention concerns a method of making a contoured internal limb that provides easy access for cannulating the contralateral gate of a prosthesis through an existing stent graft leg or limb and prostheses including the contoured internal limb.

This invention also concerns a method of making a contoured internal limb, the method including providing a tubular segment of graft material and laying the tubular segment of graft material flat. The tubular segment of graft material includes a left lateral edge, a right lateral edge, a first length extending from the left lateral edge to the right lateral edge, and a second length extending from a proximal end to a distal end of the tubular segment. The method also includes contouring a proximal portion of the contoured internal limb from the tubular segment. The proximal portion includes a first length smaller than the first length of the tubular segment and a second length extending from the proximal end of the tubular segment and along a portion of the second length of the tubular segment. The method also includes contouring a middle portion of the contoured internal limb from the tubular segment. The middle portion includes two sections, the first section extending at an angle from the proximal portion to the right lateral edge of the tubular segment, and the second section extending from the first section and along the right lateral edge of the tubular segment for a length smaller than the second length of the proximal portion. The method also includes contouring a distal portion of the contoured internal limb from the tubular segment. The distal portion extends from the second section of the middle portion and tapers to the left lateral edge of the tubular segment to the distal end of the tubular segment. The method also includes closing a right lateral edge of the proximal portion and a right lateral edge of the first section of the middle portion, and removing the proximal, middle and distal portions of the contoured internal limb from the tubular segment and maintaining the second section of the middle portion as circumferentially continuous.

The invention also concerns a method of making a contoured internal limb for insertion into a fenestration of a prosthesis including providing a flattened tubular segment of graft material including a left lateral edge, a right lateral edge, a width extending from the left lateral edge to the right lateral edge, and a length extending from a proximal end to a distal end of the tubular segment. The method also includes contouring a proximal portion of the contoured internal limb from the tubular segment. The proximal portion includes a width smaller than the width of the tubular segment and a length extending from the proximal end of the tubular segment and along a portion of the length of the tubular segment. The method also includes contouring a middle portion of the contoured internal limb from the tubular segment. The middle portion extends from the proximal portion to the right lateral edge of the tubular segment and along the right lateral edge of the tubular segment for a length smaller than the length of the proximal portion. The method also includes contouring a distal portion of the contoured internal limb from the tubular segment. The distal portion extends from the middle portion and tapers to the left lateral edge of the tubular segment to the distal end of the tubular segment to conform to the fenestration of the prosthesis. The method also includes closing a right lateral edge of the proximal portion and the section of the middle portion extending from the proximal portion to the right lateral edge of the tubular segment. The method further includes removing the proximal, middle and distal portions of the contoured internal limb from the tubular segment and maintaining the section of the middle portion that extends along the right lateral edge of the tubular segment as circumferentially continuous, inserting the proximal portion of the contoured internal limb into the fenestration of the prosthesis, and connecting the distal portion of the contoured internal limb to the fenestration of the prosthesis.

This invention also concerns a bifurcated endovascular prosthesis including a tubular main body having a diameter, a proximal end, a distal end, an internal lumen extending from the proximal end to the distal end, an anterior side, a posterior side, the anterior and posterior sides being opposite each other circumferentially around the internal lumen. The prosthesis also includes a first limb extending from the distal end of the main body, and the first limb having a diameter less than the diameter of the main body. The first limb also has a proximal end and a distal end. The prosthesis also includes a fenestration adjacent to the proximal end of the first limb, and the fenestration being disposed on the second side between the anterior and posterior sides. The prosthesis further includes a second limb extending within the internal lumen from fenestration toward the proximal end of the main of the tubular main body, and the fenestration has a substantially diamond shape and a nonlinear profile. The second limb extends into the lumen longitudinally along and circumferentially around the internal lumen.

The accompany drawings, which are incorporated herein and constitute part of this specification, and, together with the general description given above and the detailed description given below, serve to explain features of the present invention.

BRIEF DESCRIPTION OF THE DRAWINGS

In the drawings:

FIG. 1 shows a perspective view of a tubular segment of graft material

FIG. 2 shows a flattened side view of the tubular segment of graft material of FIG. 1;

FIG. 3 shows a flattened side view of the tubularsegment of graft lateral of FIG. 1;

FIG. 4 shows a perspective view of a contoured internal limb;

FIG. 5 shows a perspective view of the contoured internal limb of FIG. 4;

FIG. 10 shows a front view of the contoured internal limb of FIG. 5 inserted within the prosthesis according to the first embodiment;

FIG. 11 shows a side view of the contoured internal limb of FIG. 5 inserted within the prosthesis according to the first embodiment;

FIG. 19 shows a front view of the contoured internal limb of FIG. 5 inserted within the prosthesis according to the second embodiment;

FIG. 20 shows a side view of the contoured internal limb of FIG. 5 inserted within the prosthesis according to the second embodiment.

DETAILED DESCRIPTION OF THE DRAWINGS AND THE PRESENTLY PREFERRED EMBODIMENTS

In the present disclosure, the term "proximal" refers to a direction that is generally closest to the heart during a medical procedure, while the term "distal" refers to a direction that is farthest from the heart during a medical procedure.

The term "fenestration" refers to an opening provided through a surface of a prosthesis from the interior of the prosthesis to the exterior of the prosthesis. A fenestration may have any one of a variety of geometries including circular, semi-circular, oval, oblong, diamond, or other geometries.

The term "prosthesis" refers to any device for insertion or implantation into or replacement for a body part or a function of that body part. The term also may refer to a device that enhances or adds functionality to a physiological system. The term prosthesis may include, for example and without limitation, a stent, stent-graft, filter, valve, balloon, embolization coil, and the like.

Figure 6:
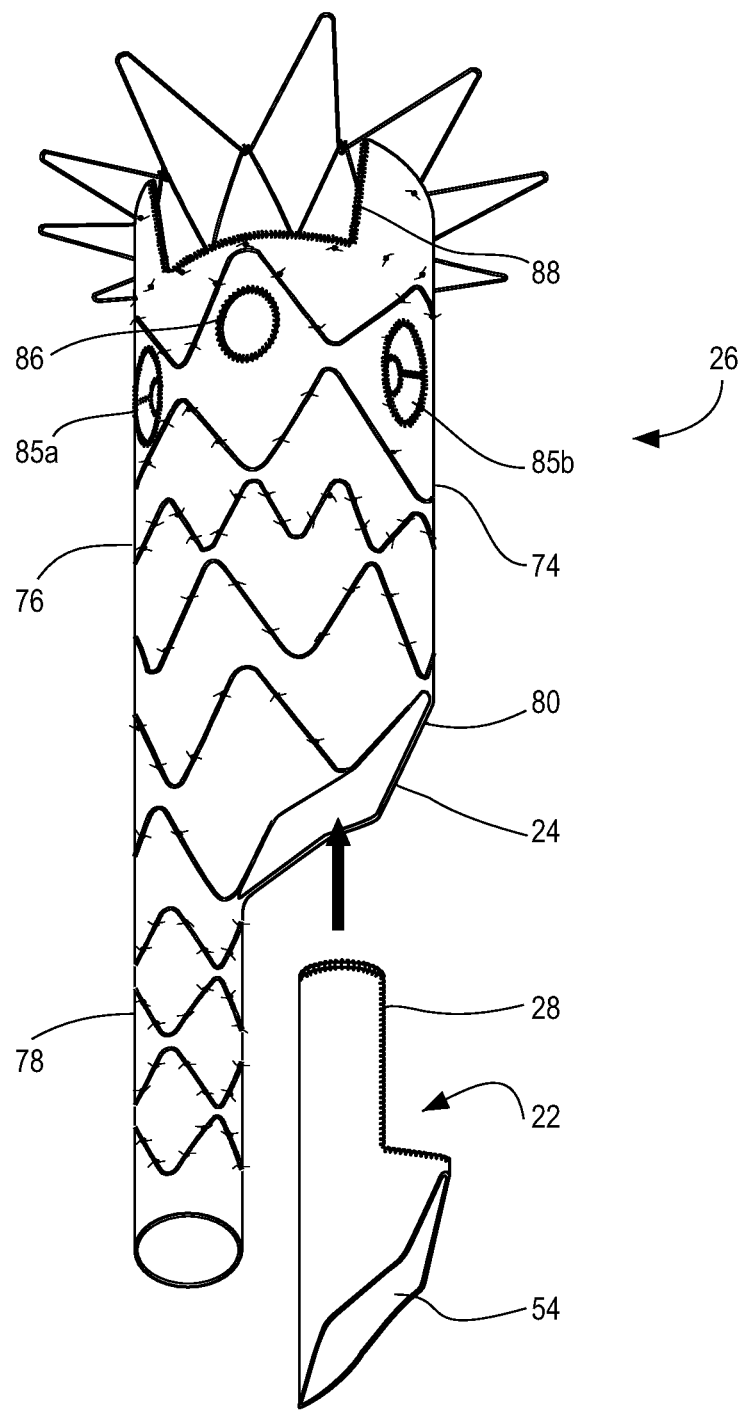
FIG. 6 shows a perspective view of inserting the contoured internal limb of FIG. 5 into a prosthesis.
Figure 12:
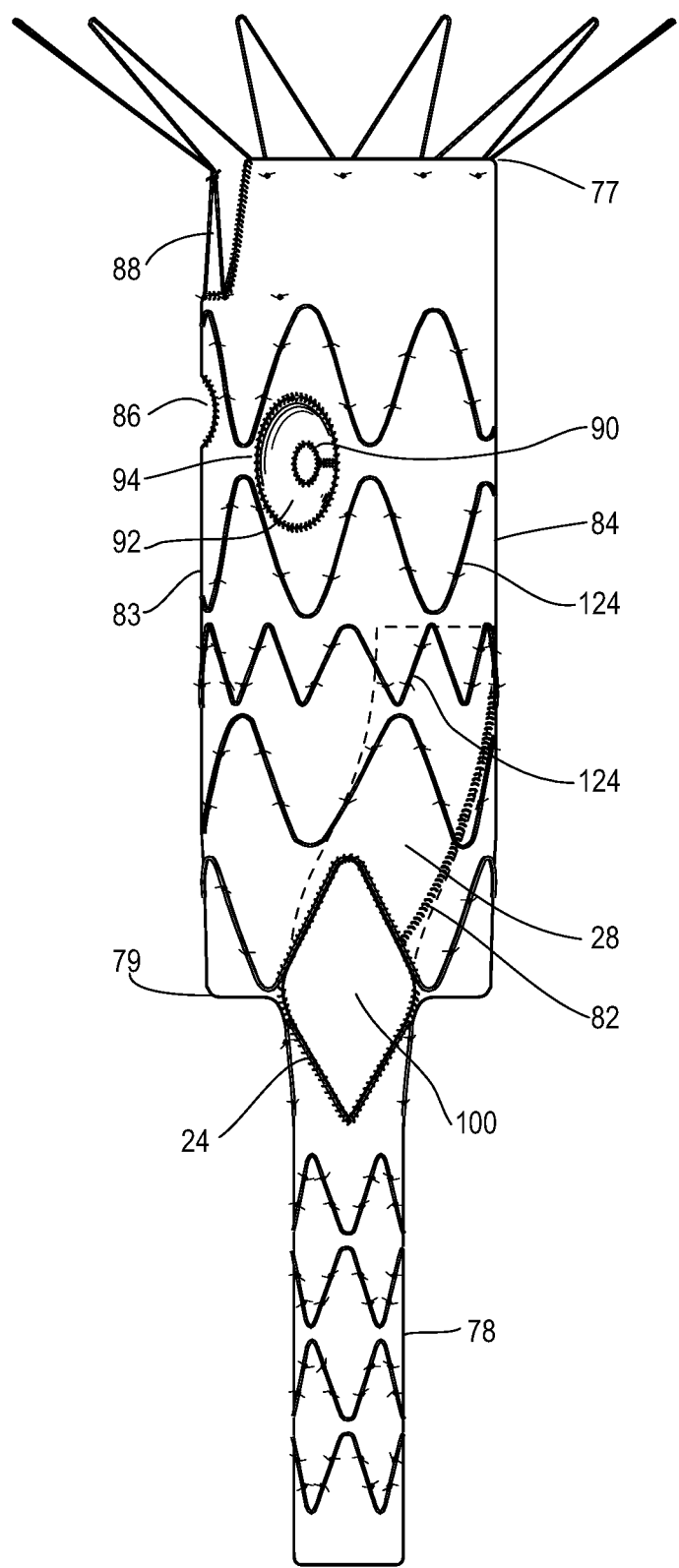
FIG. 12 shows another side view of the contoured internal limb of FIG. 5 inserted within the prosthesis according to the first embodiment.

FIG. 1 shows a tubular segment 10 of graft material. The tubular segment 10 includes a tubular body 12, a diameter 14, a proximal end 16, a distal end 18, and a length 20. The tubular segment 10 is provided to make a contoured internal limb 22, as shown in FIG. 5, from a single tubular piece of material. The contoured internal limb 22 is made to be inserted into a fenestration 24 of a prosthesis 26, such as a diamond fenestration, as shown in FIGS. 6 and 12.

The prosthesis 26 may include a bifurcated stent graft with one external distal leg and the fenestration 24 on opposing sides. Some bifurcated stent grafts may include two external distal legs; however, the bifurcated stent graft in the present disclosure includes one external distal leg and the fenestration 24. Although the fenestration 24 is described as a diamond shaped fenestration, the disclosure is not so limited. In other examples, the fenestration 24 of the prosthesis 26 may include circular, semi-circular, oval, oblong, or other geometries, and the diamond shape may include a geometry of a diamond, rhombus or parallelogram shape with oblique angles or non-oblique angles, sides with equal or varying lengths, or approximate geometries or the same, e.g. a diamond shape with rounded corners or a diamond shape that may include minor sides in addition to the four main sides, and such examples are within the scope of this disclosure. The graft material of the tubular segment 10 may include a flexible material, such as polytetrafluoroethylene (PTFE) or expanded PTFE (ePTFE), a polyester material, or other materials that allow for a seal with the prosthesis 26. The material allows an internal limb 28 of the contoured internal limb 22 to be easily expanded and collapsed.

To make the contoured internal limb 22, the tubular segment 10 may be tailored to contour the shape of the contoured internal limb 22. As shown in FIGS. 2-3, the tubular segment 10 may be laid flat along its length 20 to create a left lateral edge 30 and a right lateral edge 32 of the tubular segment 10. When the tubular segment 10 is flattened out to create the contoured internal limb 22, the tubular segment widens and has a width 15.

The tubular segment 10 may be then partitioned into three sections along the length 20 of the tubular segment 10, as shown in FIG. 2. The three sections include a proximal section 34, a middle section 36, and a distal section 38. The proximal section 34 extends from the proximal end 16 of the tubular segment 10 for a first length 40. The first length 40 may be approximately 20 mm and may be greater or less than 20 mm. As described previously, the contoured internal limb 22 is provided to be inserted into the prosthesis 26. The prosthesis 26 may be inserted into an original or existing bifurcated prosthesis that needs repair. The contoured internal limb 22 allows for stenting of a stent graft leg through the existing bifurcated prosthesis and then through the contoured internal limb 22. Therefore, the length of the contoured internal limb 22 that mates with the stent graft leg may be approximately equal, which provides the seal necessary to exclude leakage between the stent graft left and the contoured internal limb 22. Thus, the first length 40 may vary to be long enough to create the seal between the stent graft leg and the contoured internal limb, yet also be of a length such to avoid any fenestrations for the visceral arteries in the original bifurcated stent graft.

The middle section 36 extends from the proximal section 34 for a second length 42 that is smaller than the first length 40 of the proximal section 34. The second length 42 may be minimal, such as ranging from approximately 1 mm to 4 mm. The second length 42 may be less than approximately 1 mm but greater than approximately 0 mm. The second length 42 must be sufficient to allow for a section that provides circumferential continuity, to support the integrity of the internal limb 28, and to provide a section for connecting the proximal section with the circumferentially continuous section of the middle section 36. Thus, the integrity of the fabric and the manufacturing process may also affect the second length 42.

The distal section 38 extends from the middle section 36 for a third length 44. The third length 44 may be longer than the first length 40 and also may be longer than the second length 42. The third length 44 may be approximately 30 mm to 35 mm. The third length 44 may vary based on the size of the fenestration 24 of the prosthesis 26 in order to mate the distal section 38 with the fenestration 24. The first, second and third lengths 40, 42, 44 cooperatively are equal to the length 20 of the tubular segment 10.

FIG. 2 shows a contour 46 of the contoured internal limb 22 on the flattened tubular segment 10. A proximal portion 48 of the contoured internal limb 22 is formed from the proximal section 34 of the tubular segment 10. The proximal portion 48 of the contoured internal limb 22 has a width 50 that is smaller than the width 15 of the tubular segment 10. The width 50 may be approximately 19 mm and may be less or greater than 19 mm depending on the size of the prosthesis 26. As previously described, when the tubular segment 10 is flattened out or otherwise laid flat to create the contoured internal limb 22, the tubular segment 10 widens from the diameter 14 to the width 15. Thus, if the intended inner diameter 17 of the contoured internal limb 22, as shown in FIG. 5, is approximately 12 mm, then the width 50 of the proximal portion 48 of the contoured internal limb 22 when laid flat may be approximately 19.3 mm. The width 50 of the proximal portion 48 will vary depending on the intended diameter 17 of the contoured internal limb 22, which varies based on the diameter of the stent graft leg that mates with the contoured internal limb 22 and that will be inserted through the existing bifurcated prosthesis and through the contoured internal limb 22. Thus, if the stent graft leg has a diameter of approximately 11 mm, then the intended diameter 17 of the contoured internal limb 22 may be approximately 11 mm, 12 mm or 13 mm. The intended inner diameter 17 of the contoured internal limb 22 may range from approximately 11 mm to 13 mm. The length of the proximal portion 48 is the same as the first length 40 of the proximal section 34 of the tubular segment 10. Thus, the contour 46 of the proximal portion 48 of the contoured internal limb 22 is a line that begins at a distance away from the left lateral edge 30 of the tubular segment 10 that is equal to width 50, and then extends away from the proximal end 16 of the tubular segment 10 toward the distal end 18 of the tubular segment 10 for a distance equal to the first length 40 of the proximal section 34 of the tubular segment 10.

A middle portion 52 of the contoured internal limb 22 is formed from the middle section 36 of the tubular segment 10. The middle portion 52 of the contoured internal limb 22 forms the connection between the internal limb 28 of the contoured internal limb 22 and a fenestration 54 of the contoured internal limb 22. As shown in FIG. 2, the contour 46 of the middle portion 52 of the contoured internal limb 22 comprises two sections. The first section 64 extends from the contour 46 of the proximal portion 48 of the contoured internal limb 22 and tapers distally to the right lateral edge 32 of the tubular segment 10 or alternatively, extends straight from the contour 46 of the proximal portion 48 of the contoured internal limb 22 to the right lateral edge 32 of the tubular segment 10, such that the contour 46 of the middle portion 52 is initially perpendicular to the contour 46 of the proximal portion 48 of the contoured internal limb 22.

The first section 64 of the middle portion 52 is distal to the proximal portion 48 of the contoured internal limb 22 and proximal to the second section 62 of the middle portion 52. The second section 62 of the middle portion 52 then extends along the right lateral edge 32 for a length 56 that is smaller than or equal to the second length 42 of the middle section 36 of the tubular segment 10. Thus, at its widest part, the middle portion 52 of the contoured internal limb 22 includes a width 58 that is equal to the width 15 of the flattened tubular segment 10. The width 58 may be approximately 16 mm and may be greater than 16 mm depending on the size of the prosthesis 26.

A distal portion 60 of the contoured internal limb 22 is formed from the distal section 38 of the tubular segment 10. The distal portion 60 includes the fenestration 54 of the contoured internal limb 22. The contour 46 for the distal portion 60 extends from the contour 46 of the middle portion 52 of the contoured internal limb 22 and the right lateral edge 32 of the tubular segment 10 and then tapers to the left lateral edge 30 and to the distal end 18 of the tubular segment 10. The contour 46 of the distal portion 60 follows a curvature similar to multiple parabolic segments flipped and abutted to create inflection points as shown in FIG. 2. Thus, the width of the distal portion 60 varies along the length of the distal portion 60, which is equal to the length 44 of the distal section 38 of the tubular segment 10.

The contour 46 of the distal portion 60 creates an opening for the fenestration 54 of the contoured internal limb 22 that is large enough and shaped appropriately to connect with the fenestration 24 of the prosthesis 26. Although the contour 46 of the distal portion 60 is described as to conform to the shape of a diamond shaped fenestration, the disclosure is not so limited. In other examples, the contour 46 of the distal portion 60 may vary to conform to the shape of a complex curve of a fenestration, scallop, or stent strut at the distal end of any branch design, and such examples are within the scope of this disclosure. As described previously, the fenestration 24 of the prosthesis 26 may a variety of shapes, and the contour 46 of the distal portion 60 conforms to the shape of the fenestration 24. Also, when the fenestration 54 of the contoured internal limb 22 is diamond shaped, the diamond shape of the contour 46 of the distal portion 60 may include a diamond, rhombus or parallelogram shape with oblique angles or non-oblique angles and sides with equal or varying lengths. In view of several factors, including without limitation the length of any stent struts of the prosthesis 26, any involvement of the stent struts near edges of the fenestration 24, the multiple sections of contour to form the contoured internal limb 22, and the shape of the contour of the contoured internal limb 22, the contour 46 of the distal portion 60 may vary.

After creating the contour 46 of the contoured internal limb 22 on the tubular segment 10, the right lateral edge of the proximal portion 48 of the contoured internal limb 22 and the right lateral edge of the first section 64 of the middle portion 52 are closed by laser or heat sealing, sewing or stitching 66, as shown in FIG. 3. The right lateral edge of the proximal portion 48 and the right lateral edge of the first section 64 of the middle portion 52 are dosed to make the proximal portion 48 and middle portion 52 circumferentially continuous. The stitching 66 along the proximal portion 48 creates the lumen 68 of the internal limb 28 of the contoured internal limb 22. The stitching 66 along the proximal portion 48 and the first section 64 of the middle portion 52 may be continuous to form a single seam.

After closing the right lateral edge of the proximal portion 48 and the right lateral edge of the first section 64 of the middle portion 52, the contoured internal limb 22 may be removed from the tubular segment 10. For example, the proximal portion 48 may be cut along the right side of the stitching 66 to maintain the integrity of the proximal portion 48. Then, the first section 64 of the middle portion 52 may be cut along the right side of the stitching 66 to maintain the integrity of the middle portion 52. Thus, the stitching must be maintained. Excess fabric may extend beyond the stitching 66 of the proximal portion 48 and the first section 64 of the middle portion 52 and may be removed by further cutting or removal means. The excess fabric may be heat sealed to prevent any unraveling of the fabric. The right lateral edge of the second section 62 of the middle portion 52 is maintained to be circumferentially continuous and not cut open. The distal portion 60 may then be cut along the contour 46, as shown in FIG. 4. Thus, only the distal portion 60 of the contoured internal limb 22 is cut open when the contoured internal limb 22 is removed from the tubular segment 10. The order of cutting may also be reversed, beginning with the distal portion 60.

Alternatively, the contoured internal limb 22 may be removed from the tubular segment 10 before the right lateral edge of the proximal portion 48 and the right lateral edge of the first section 64 of the middle portion 52 are removed. In this embodiment, the second section 62 of the middle portion 52 is maintained as circumferentially continuous, which avows the contoured internal limb 22 to maintain its tubular shape after removal from the tubular segment 10. The right lateral edge of the proximal portion 48 and the right lateral edge of the first section 64 of the middle portion 52 are then dosed by laser or heat sealing, sewing or stitching 66.

The right lateral edges of the distal portion 60 of the contoured internal limb 22 form the large diagonal opening of the fenestration 54, as shown in FIGS. 4-5. Thus, the distal portion 60 of the contoured internal limb 22 does not include any sewing or stitching prior to its attachment to the main body of the graft.

The contoured internal limb 22 may also include a ring 70 positioned at the proximal end 72 of the contoured internal limb 22. The ring 70 maintains the patency of the lumen 68 of the internal limb 28 and provides structure to the internal limb 28. The ring 70 also allows for something to seal against, while also minimizing packing density because it will collapse during loading of the contoured internal limb 22. The material of the ring 70 may include nitinol or other shape memory or elastic metal. As shown in FIGS. 4-5, the ring 70 may be sewn or stitched to the proximal end 72 of the contoured internal limb 22. The ring may have a pure circular or other shape, which may aid in support, packing, and/or collapse.

The contoured internal limb 22 may be free of any stents, such as the Z-stent or Gianturco stent design. Although the contoured internal limb 22 is described as free of any stents, the disclosure is not so limited. In other examples, the contoured internal limb 22 may include a stent pattern such as the Z-stent or Gianturco stent design, and such examples are within the scope of this disclosure. Each Z-stent may include a series of substantially straight segments or struts interconnected by a series of bent segments or bends. The bent segments may include acute bends or apices. The Z-stents are arranged in a ZigZag configuration in which the straight segments are set at angles relative to one another and are connected by the bent segments. This design provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. Furthermore, in complex anatomical situations, external stents may have the potential to become intertwined with the wires or other devices utilized to ensure branch vessel access, sealing, and fixation. Thus, in some instances, it may be desirable to affix some of the stents to the external and/or internal surfaces of the contoured internal limb 22.

The proximal portion 48 of the contoured internal limb 22 is then inserted into the fenestration 24 of the prosthesis 26, as shown in FIG. 6, and into the body of the prosthesis 26. The contoured internal limb 22 may be positioned within the prosthesis 26 to adapt to the configuration of the prosthesis 26.

For example, as shown in FIGS. 6-13 and 17-21, the prosthesis 26 includes a stent graft 74 that includes a tubular main body 76 including a proximal end 77, a distal end 79, and an internal lumen 81 extending from the proximal end 77 to the distal end 79 of the tubular main body 76. The stent graft 74 also includes a limb 78 extending from the distal end 79 of the tubular main body 76. The tubular main body 76 also includes a frustoconical midsection 80 adjacent to the limb 78. The fenestration 24 of the prosthesis 26 is located in the frustoconical midsection 80. The limb 78 of the main stent graft body 74 has a tubular shape and extends distally from the distal end 79 of the tubular main body 76, as shown in FIG. 6. The limb 78 can be sized and dimensioned for insertion into an iliac artery or existing stent graft limb/leg/body. The prosthesis 26 may also include a plurality of stents 124, as described previously.

The tubular main body 76 of the stent graft 74 includes an anterior side 83 and a posterior side 84. The anterior and posterior sides 83, 84 are opposite to each other circumferentially around the internal lumen 81. The anterior side 83 may extend circumferentially around approximately half of the circumference of the tubular main body 76. The posterior side 84 may extend circumferentially around approximately the other half of the circumference of the tubular main body 76. The posterior side 84 of the tubular main body 76 may be positioned opposite the anterior side 83 with respect to the circumference of the tubular main body 76. In other words, a plane may be defined to include the longitudinal axis of the tubular main body 76. The anterior side 83 may be positioned on one side of the plane, and the posterior side 84 may be positioned on the opposite side of the plan from the anterior side 83. The anterior side 83 and the posterior side 84 may cooperatively form the tubular main body 76.

Figure 14:
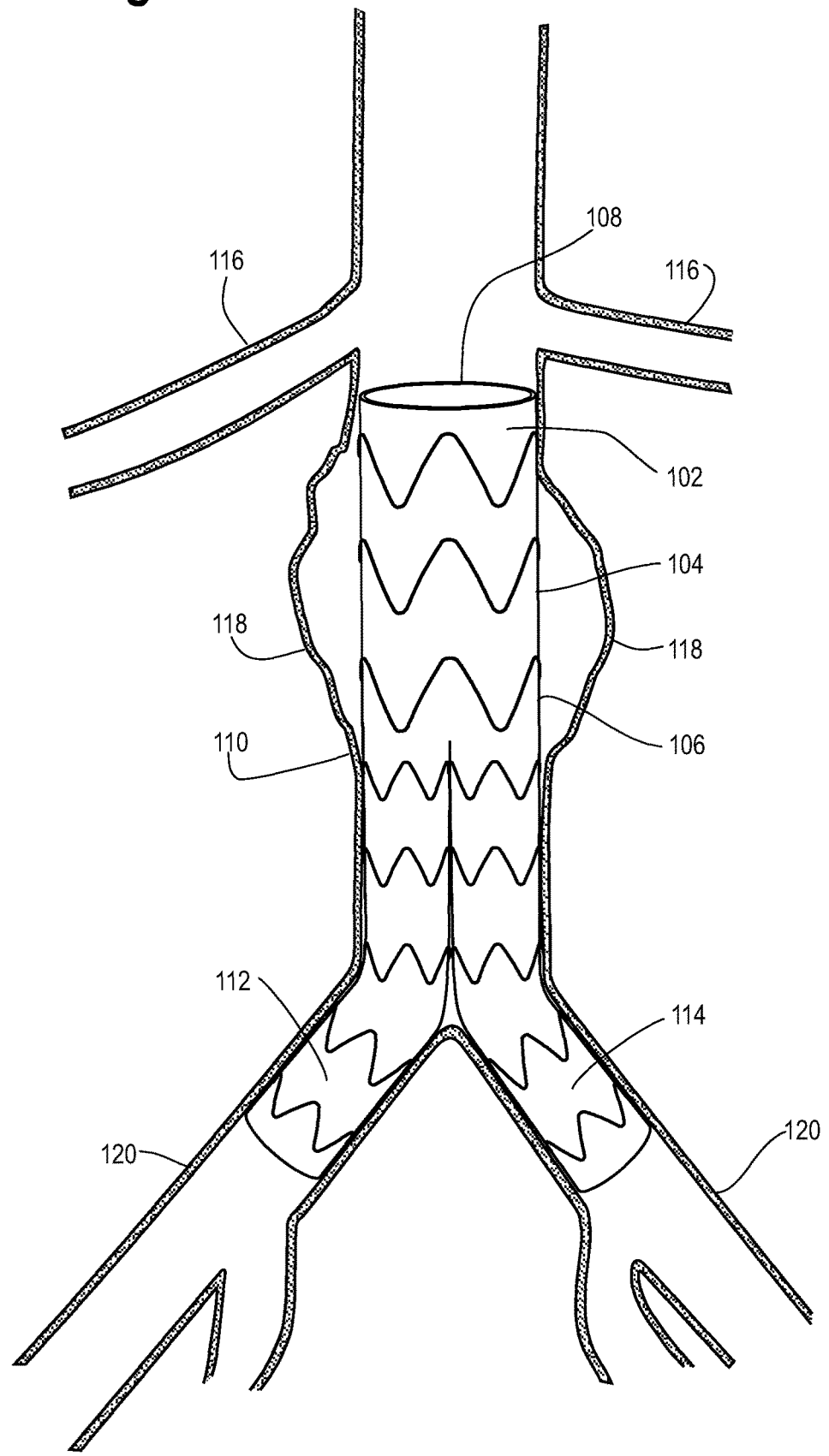
FIG. 14 shows a perspective view of an existing prosthesis inside a patient's body that needs repair.
Figure 15:
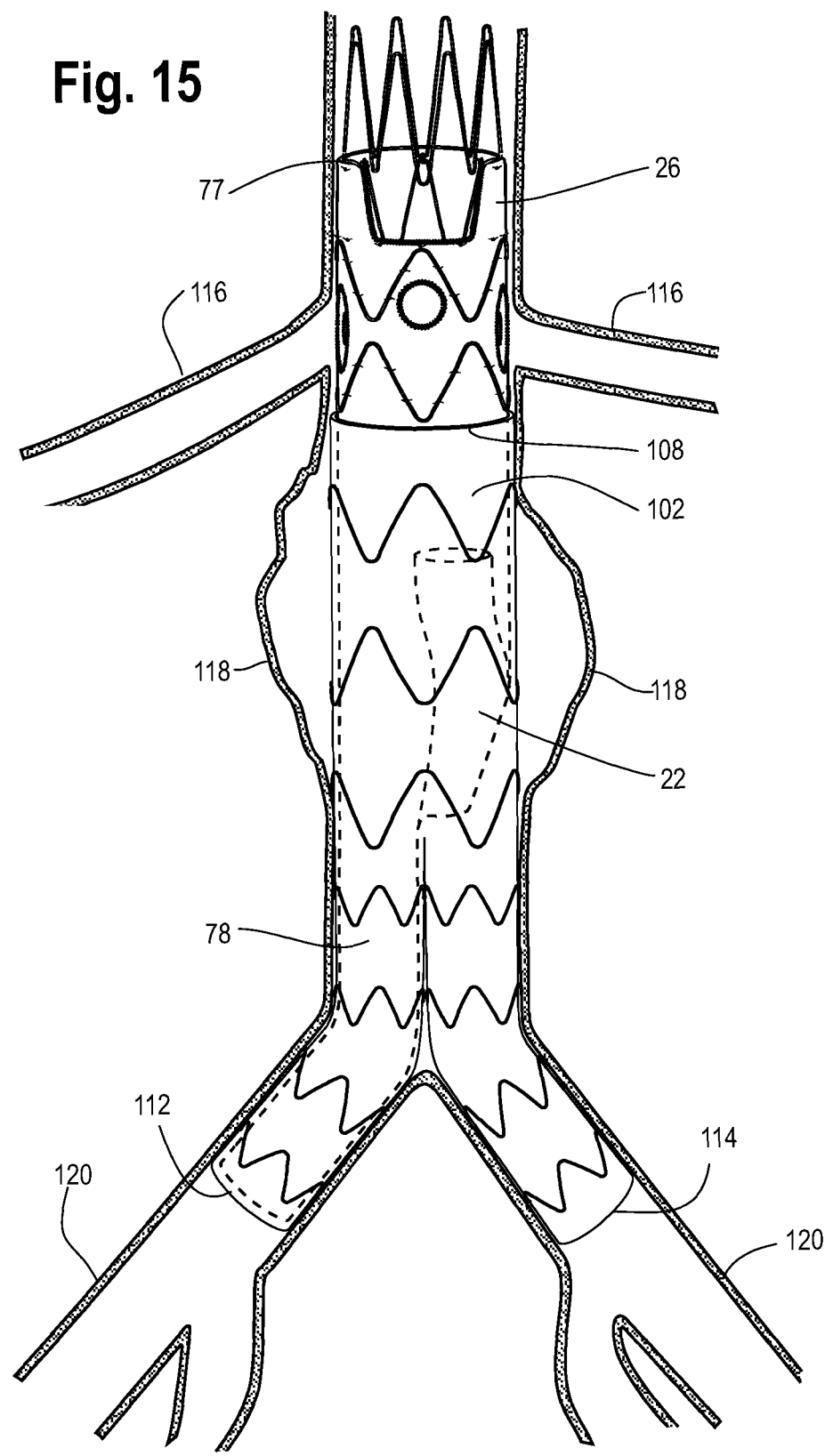
FIG. 15 shows a perspective view of the prosthesis with the contoured internal limb inserted within the existing prosthesis inside a patient's body.
Figure 16:
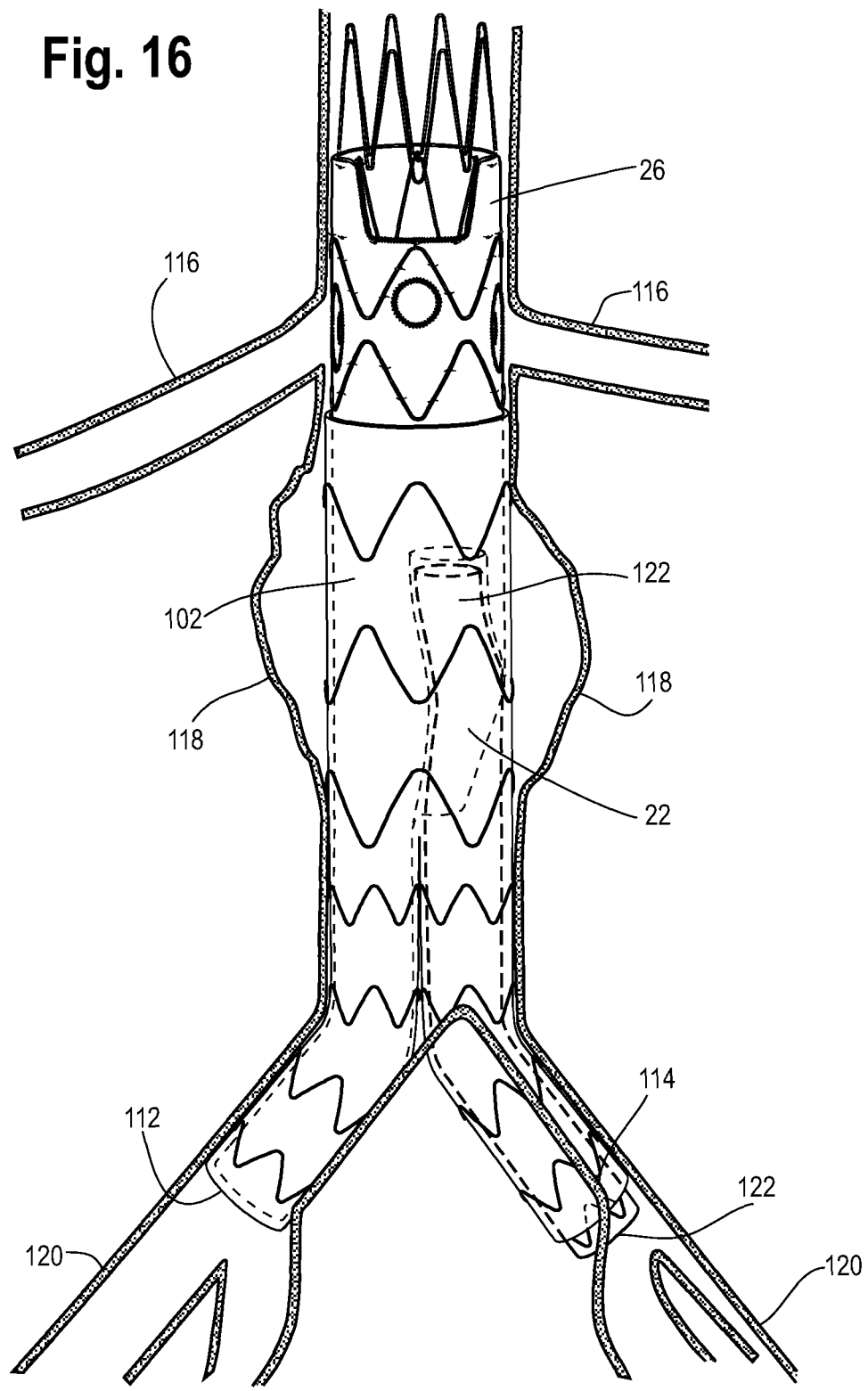
FIG. 16 shows a perspective view of an iliac limb extension inserted into the contoured internal limb of the prosthesis.
Figure 17:
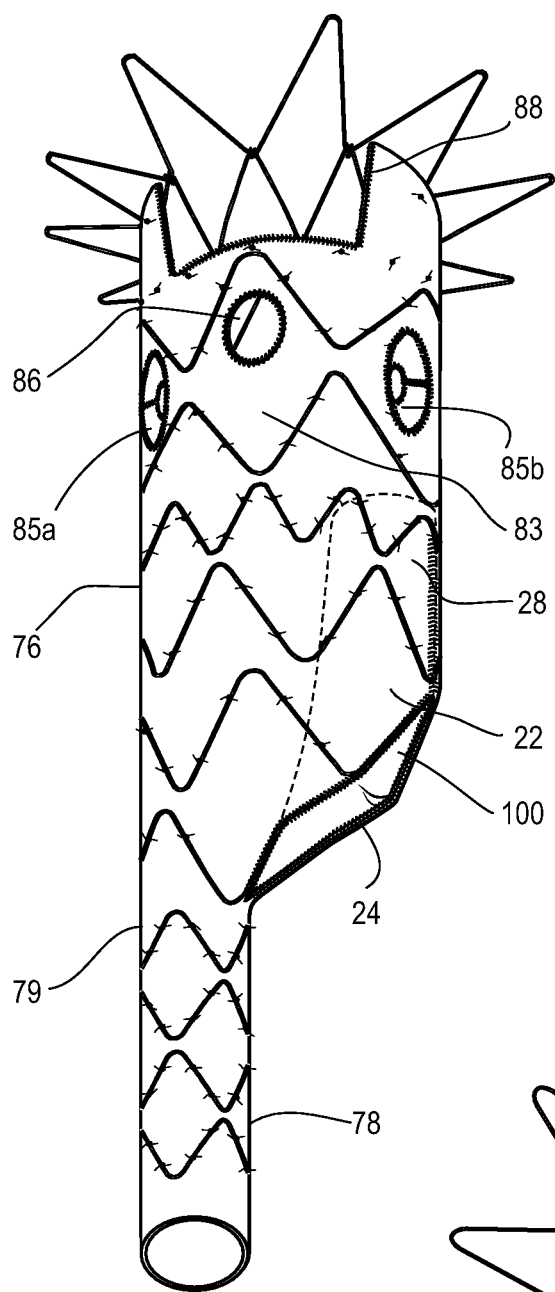
FIG. 17 shows a perspective view of the contoured internal limb of FIG. 5 inserted within the prosthesis according to a second embodiment.

The tubular main body 76 may include fenestrations that may be pivotable or non-pivotable. The tubular main body 76 may include two pivotable fenestrations 85, a non-pivotable fenestration 86, and a scallop 88 as shown in FIGS. 6-7, 17, and 19-20. Although the tubular main body 76 is described as including two pivotable fenestrations 85 and a non-pivotable fenestration 86, the disclosure is not so limited. In other examples, any of the fenestrations may be pivotable or non-pivotable, and such examples are within the scope of this disclosure. The pivotable fenestrations 85 may be positioned on the tubular main body 76 to radially align with, for example, the renal arteries 116, as shown in FIGS. 14-16. The non-pivotable fenestration 86 may be positioned on the tubular main body 76 to radially align with, for example, the superior mesenteric artery (SMA). The scallop 88 may be configured to align with the celiac artery. It will be recognized by one of ordinary skill in the art that the prosthesis 26 may include any number of openings or fenestrations of any type. Also, the fenestrations may be arranged on the prosthesis 26 in any manner. Preferably, the fenestrations may be arranged to correspond to a particular position within the anatomy into which the prosthesis 26 is intended to be placed.

Figure 8:
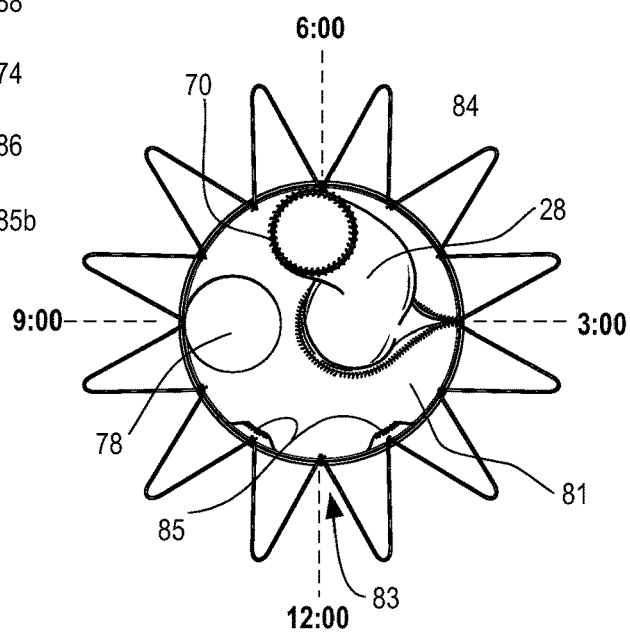
FIG. 8 shows a top view of the contoured internal limb of FIG. 5 inserted within the prosthesis according to the first embodiment.

The pivotable fenestrations 85 may include an inner perimeter 90 surrounding the fenestration 85, a band 92 surrounding the inner perimeter 90, and an outer perimeter 94 surrounding the band 92, as shown in FIG. 12. The outer perimeter 94 may have a diameter that is greater than a diameter of the inner perimeter 90. The inner perimeter 90, the band 92, and the outer perimeter 94 may be substantially concentric with one another if brought into the same plane, for example, the surface plane of the graft. The inner perimeter 90, the band 92, and the outer perimeter 94 may form an extension having a hemispherical shape, resembling a dome, or a frustoconical cone extending from the surface of the tubular main body 76. The fenestration 85 may be positioned at the peak or top of the extension. The fenestration 85 may be placed in a concave orientation or a convex orientation. In the concave orientation, the extension may extend into the internal lumen 81 of the tubular main body 76 as shown in FIG. 8. In the convex orientation, the extension may extend away from the internal lumen 81. The pivotable fenestration 85 may be movable between the concave orientation and the convex orientation. The pivotable fenestration 85 also may be placed in any position between the concave orientation and the convex orientation. For example, the band 92 may be folded, bent, gathered, pleated, or otherwise manipulated such that the fenestration 85 is generally aligned with the surface plane of the tubular main body 76.

The outer perimeter 94 of the pivotable fenestration 85 may be affixed to the tubular main body 76 by any attachment method including suturing circumferentially about an aperture disposed through the tubular main body 76. The band 92 may be sufficiently flexible to permit the fenestration 85 to move such that a branch prosthesis disposed in the fenestration 85 may be oriented upwardly, downwardly, laterally, diagonally, and the like relative to the surface of the tubular main body 76. In some examples, the band 92 may permit the fenestration 85 to move up to about 180 degrees relative to the surface plane of the tubular main body 76. Accordingly, the pivotable fenestration 85 may allow the prosthesis 26 to be used in a variety of patients due to its ability to adapt to the variance in the positioning of the diseased branch vessels. For example, if a branch vessel is or becomes offset longitudinally or axially from a pivotable fenestration 85, the pivotable fenestration 85 may pivot the prosthesis 26 in the necessary direction and to the necessary degree to maintain the prosthesis 26 in place in the branch vessel.

An important aspect of the fenestrations 85, 86 and the scallop 88 on the prosthesis 26 is to maintain blood flow to the visceral vessels, including the renal arteries 116, the superior mesenteric artery, and the celiac artery, after implantation of the prosthesis 26 within the abdominal aorta. In some instances, the fenestrations 85, 86 are used to allow a prosthesis, stent, wire and other device to access the visceral vessels. When the contoured internal limb 22 is inserted through the fenestration 24 and into the internal lumen 81 of the tubular main body 76, the contoured internal limb 22 occupies a portion of the internal lumen 81. Therefore, positioning the contoured internal limb 22 within the internal lumen 81 to avoid the fenestrations 85, 86 may minimize interference within the internal lumen 81 of the tubular main body 76.

For example, the prosthesis 26 may be configured to extend between a point proximal to the renal arteries 116 and a point distal to the renal arteries 116. Thus, the scallop 88 may be configured to align with the celiac artery, the pivotable fenestrations 85 may be configured to align with the renal arteries 116, and the non-pivotable fenestration 86 may be configured to align with the superior mesenteric artery. As previously described, although the tubular main body 76 is described as including two pivotable fenestrations 85 and a non-pivotable fenestration 86, the disclosure is not so limited. In other examples, any of the fenestrations may be pivotable or non-pivotable, and such examples are within the scope of this disclosure. The scallop 88 may be positioned circumferentially on an anterior point 96 of the tubular main body 76 and longitudinally at the proximal end 77 of the tubular main body 76. The anterior point 96 may extend generally longitudinally along the tubular main body 76 and may be substantially circumferentially centered on the anterior side 83 of the tubular main body 76. The tubular main body 76 also includes a posterior point 98 that is substantially circumferentially centered on the posterior side 84 of the tubular main body 75, as shown in FIG. 11.

The non-pivotable fenestration 86 may be positioned circumferentially on the anterior point 96 of the tubular main body 76 and longitudinally distal to the scallop 88. The pivotable fenestrations 85 may be spaced from one another by a predetermined distance around the circumference of the tubular main body 76. For example, the first pivotable fenestration 85a may be configured to align with the right renal artery and may be spaced a first circumferential distance from the anterior point 96 of the tubular main body 76. The second pivotable fenestration 85b may be configured to align with the left renal artery and may be spaced a second circumferential distance from the anterior point 96 of the tubular main body 76. The first and second circumferential distances may be of substantially equal lengths in opposite directions relative to the anterior point 96 of the tubular main body 76. Alternatively, the first and second circumferential distances may be different from one another, for example, to correspond to the anatomy of a particular patient or patients. The first and second pivotable fenestrations 85a, 85b may be positioned at substantially the same longitudinal position along the tubular main body 76. Alternatively, the first and second pivotable fenestrations 85a, 85b may be offset longitudinally with respect to one another, for example, to correspond to the anatomy of a particular patient or patients. The first and second pivotable fenestrations 85a, 85b may be positioned longitudinally distal to the non-pivotable fenestration 86 and the scallop 88, as shown in FIGS. 6-7, 12, 17, and 19-20. As shown in FIGS. 6-7, 12, 17 and 19-20, the pivotable fenestrations 85a, 85b may both be positioned on the anterior side 83 of the tubular main body 76. In other examples, the pivotable fenestrations 85a, 85b may be positioned circumferentially centered between the anterior and posterior sides 83, 84 or positioned on the posterior side 84.

The limb 78 and the fenestration 24 are spaced apart from one another by a predetermined distance around the circumference of the prosthesis 26. Specifically, the limb 78 is positioned longitudinally distal to the non-pivotal fenestration 86 and spaced a circumferential distance from the anterior point 96 of the tubular main body 76. The fenestration 24 is also positioned longitudinally distal to the non-pivotal fenestration 86 and spaced a circumferential distance from the anterior point 96 of the tubular main body 76. The circumferential distance of the limb 78 and the fenestration 24 from the anterior point 96 is approximately equal. Thus, the limb 78 and the fenestration 24 may be positioned on the prosthesis 26 approximately 90 degrees from the anterior point 96 of the tubular main body 25 with respect to the circumference of the prosthesis 26 in opposite directions, or in other words, the limb 78 and the fenestration 24 may be positioned on opposite sides of the prosthesis 26 relative to the anterior point 96. For example, the limb 78 and the fenestration 24 may be circumferentially centered between the anterior and posterior sides 83, 84 of the tubular main body 25 and 180 degrees from one another with respect to the circumference of the tubular main body 25 as shown in FIGS. 8 and 18.

As shown in FIGS. 6-13, when the contoured internal limb 22 is inserted through the fenestration 24 and into the internal lumen 81 of the tubular main body 25, the internal limb 28 of the contoured internal limb 22 extends from the fenestration 24 into the internal lumen 81 and helically or circumferentially around a portion of the interior lumen 81 and then along the posterior side 84 of the tubular main body 76. In other words, as the internal limb 28 extends through the internal lumen 81 of the tubular main body 76, the internal limb 28 is positioned or otherwise rotated to initially align circumferentially with the tubular main body 76 and then extend internally along the posterior side 84 of the tubular main body 76 to avoid the pivotable fenestrations 85 and non-pivotable fenestration 86.

Figure 18:
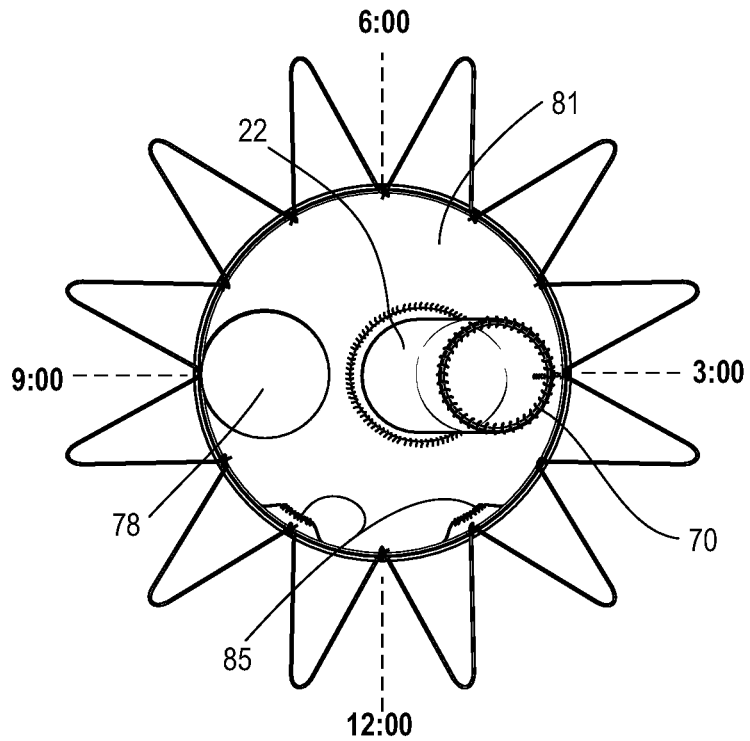
FIG. 18 shows a top view of the contoured internal limb of FIG. 5 inserted within the prosthesis according to the second embodiment.

In an alternative configuration, as shown in FIGS. 17-21, when the contoured internal limb 22 is inserted through the fenestration 24 and into the internal lumen 81 of the tubular main body 25, the internal limb 28 of the contoured internal limb 22 extends from the fenestration 24 into the internal lumen 81 and is not rotated; rather, the internal limb 28 extends through the internal lumen 81 between the anterior side 83 and the posterior side 84, as shown in FIG. 18. In other words, the internal limb 28 extends vertically through the internal lumen 81 and toward the proximal end 77 of the tubular main body 76 between the anterior side 83 and the posterior side 84 of the tubular main body 76.

Figure 13:
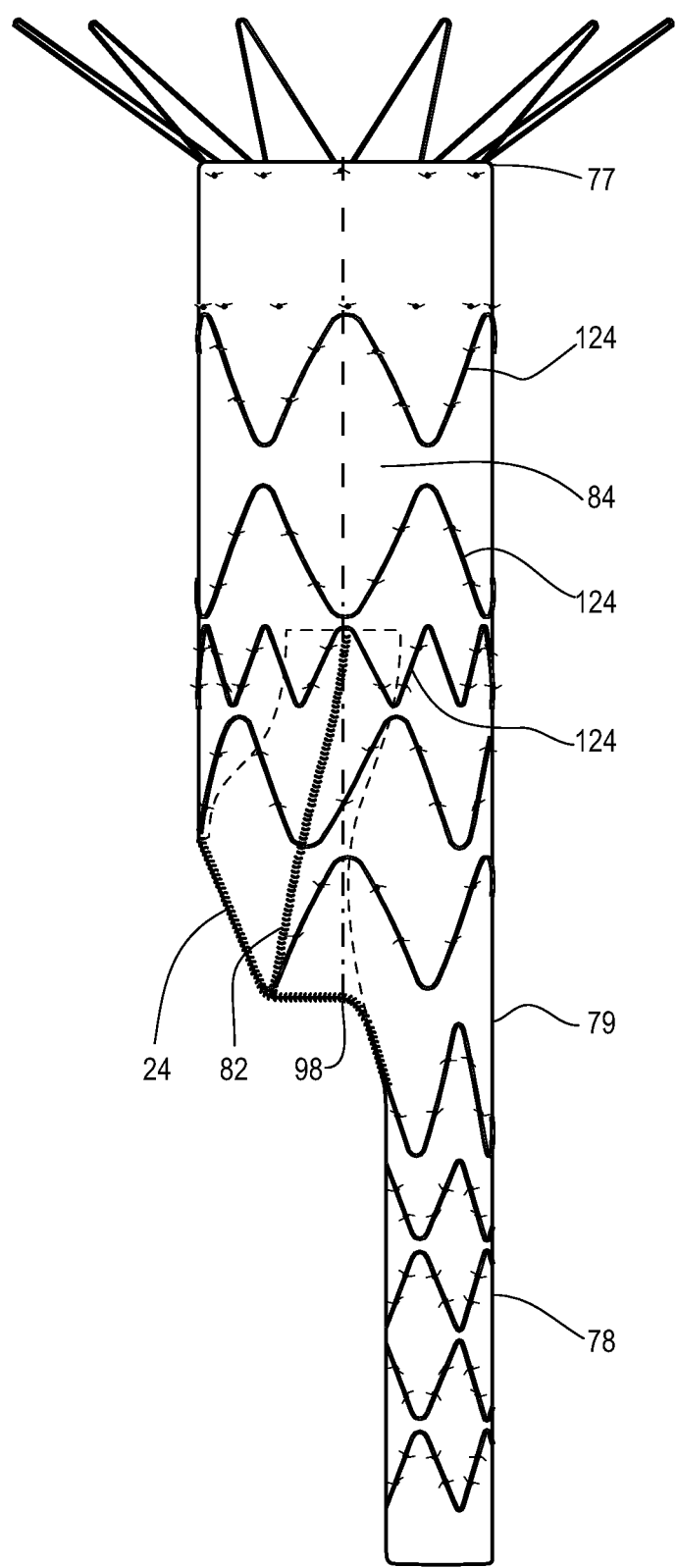
FIG. 13 shows a back view of the contoured internal limb of FIG. 5 inserted within the prosthesis according to the first embodiment.
Figure 21:
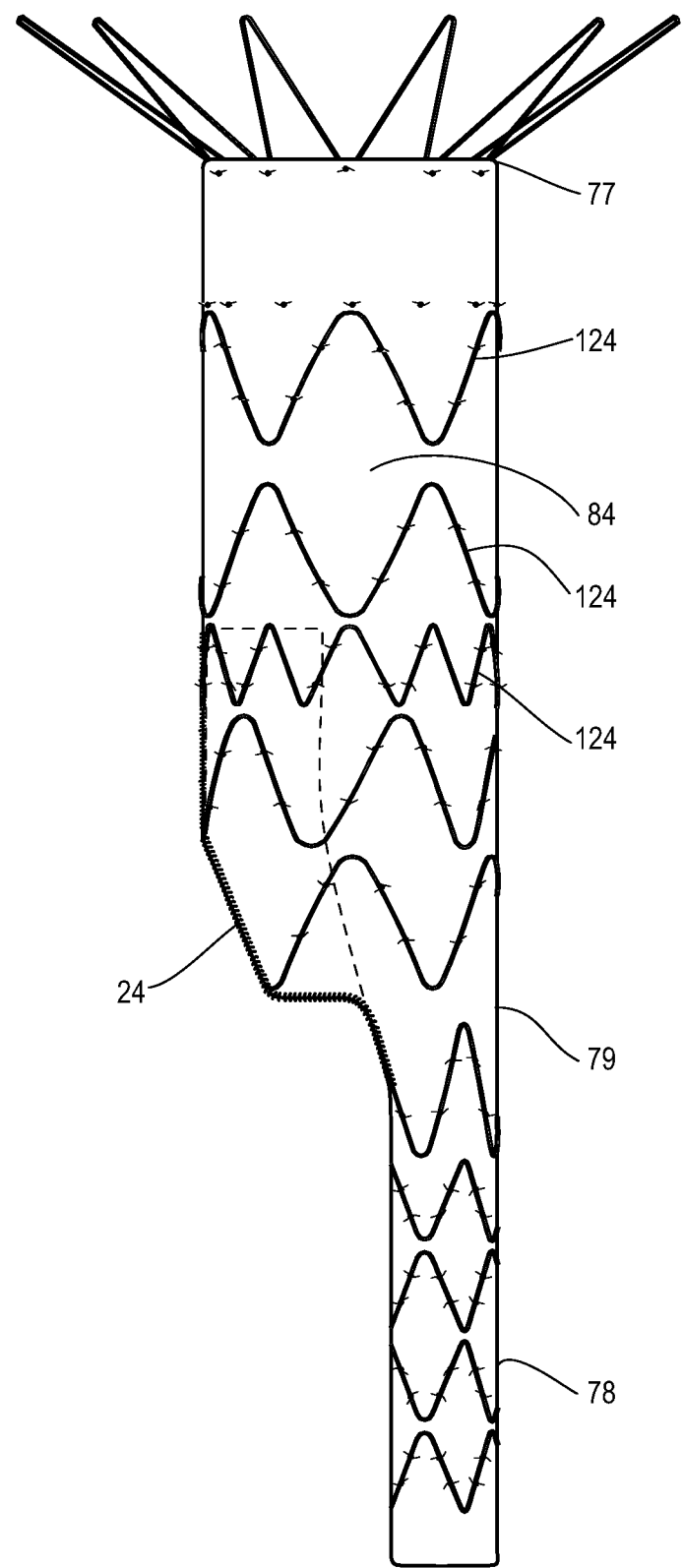
FIG. 21 shows a back view of the contoured internal limb of FIG. 5 inserted within the prosthesis according to the second embodiment.

After the contoured internal limb 22 is inserted through the fenestration 24 and into the prosthesis 26, the fenestration 54 of the distal end portion 60 of the contoured internal limb 22 may be connected to the fenestration 24 of the prosthesis 26 via laser or heat sealing, stitching or sewing. The internal limb 28 of the contoured internal limb 22 may also be sewn, sutured or stitched 82 to the main stent graft body 74 to maintain the positioning of the internal limb 28 of the contoured internal limb 22 within the prosthesis 26. The internal limb 28 is only sewn, sutured, or stitched 82 along the side of its tubular wall that is in contact with the main stent graft body 74 to ensure the internal limb 28 maintains its position and (if desired) patency within the internal lumen 81. For example, as shown in FIG. 13, when the internal limb 28 is extends helically through the internal lumen 81 and then along the posterior side 84 of the prosthesis 26, the sewing, suturing or stitching 82 of the internal limb 28 to the main stent graft body 74 may extend at an angle along the posterior side 84 of the prosthesis 26. In another embodiment, as shown in FIG. 21, the internal limb 28 may be sewn, sutured, or stitched 82 along the side of the prosthesis 26 between the anterior side 83 and the posterior side 84, such as to align with the single seam 66 of the contoured internal limb 22.

Figure 7:
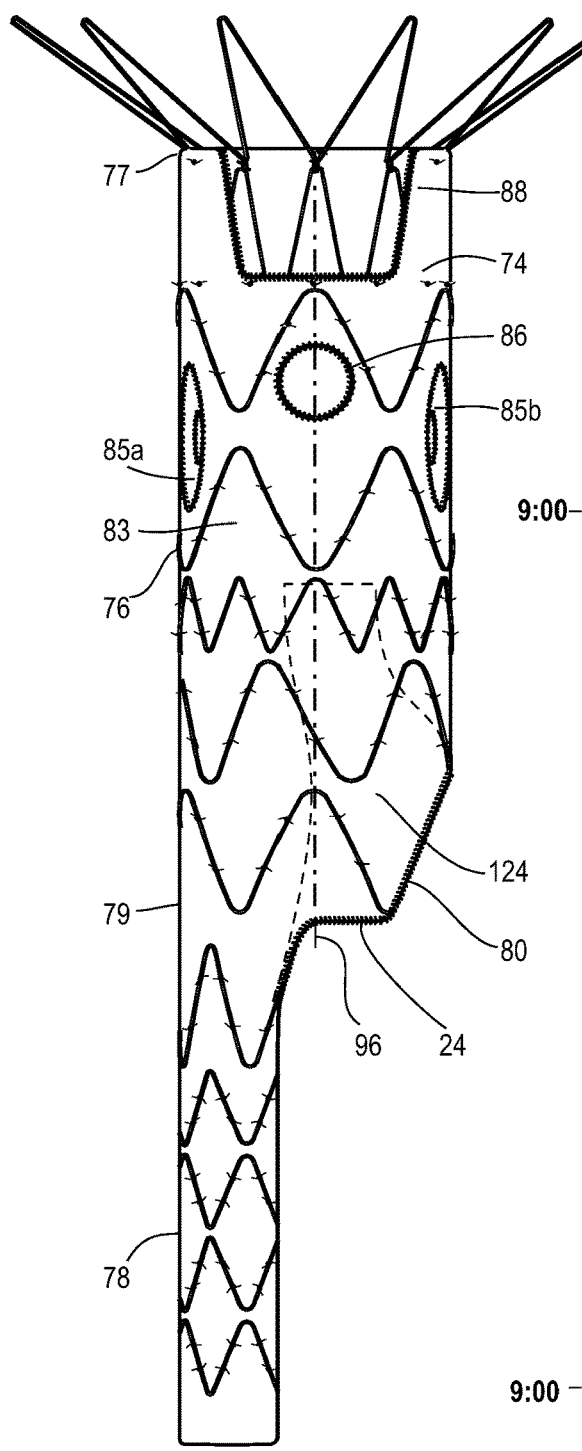
FIG. 7 shows a front view of the contoured internal limb of FIG. 5 inserted within the prosthesis according to a first embodiment.

The fenestration 24 with the contoured internal limb 22 connected to the fenestration 24 may not take its shape naturally. Thus, the contoured internal limb 22 creates a shelf-like configuration when attached to the fenestration 24 and opens the fenestration 24. For example, as shown in FIGS. 7 and 19, the proximal half of the fenestration 24 may collapse distally and lies at an angle, such as 90 degrees or greater, to the distal half of the fenestration 24. This orientation or shelf-like configuration of the fenestration 24 creates an effectively larger target for an approaching wire, catheter, dilator or other device to be easily inserted through the fenestration 24 and facilitates cannulation.

As shown in FIGS. 11-12, 17 and 20, the contoured internal limb 22 also creates a smooth seamless slope or path 100 for an approaching wire, catheter, dilator or other device to be inserted through the fenestration 24 and slide unimpeded through the fenestration 54 and the internal limb 28 of the contoured internal limb 22. As described previously, since the contoured internal limb 22 is formed from a single tubular segment 10 and includes only one continuous seam 66 along the right lateral edge of the contoured internal limb 22 of the proximal and middle portions 48, 52, the contoured internal limb 22 minimizes the areas where an approaching wire, catheter, dilator or other device may catch or snag when moving through the contoured internal limb 22. The smooth seamless slope 100 allows for ease of cannulation.

Figure 9:
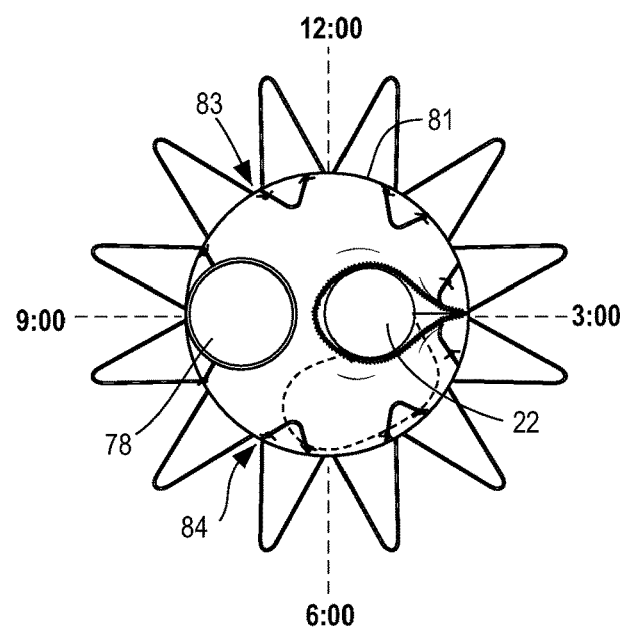
FIG. 9 shows a bottom view of the contoured internal limb of FIG. 5 inserted within the prosthesis according to the first embodiment.

The circumferential positions of the various components or features of the prosthesis 26 may be described with reference to a dock face as shown in FIGS. 8-9 and 18. For example, as shown in FIG. 8, the clock face may be positioned such that 12 o'clock corresponds to the anterior point 83 of the prosthesis 26 and 6 o'clock corresponds to the posterior point 98 of the prosthesis 26, such as looking up from a patient's distal aorta. Thus, the non-pivotable fenestration 86 and/or the scallop 88 may be positioned circumferentially at approximately 12 o'clock, i.e., along the anterior point 83 of the prosthesis 26. The pivotable fenestrations 85a, 85b may be positioned circumferentially on the prosthesis 26 between approximately 1:30 to 3:00 o'clock and between approximately 9:00 to 10:30 o'clock, respectively. For example, in FIGS. 6-12 and 17-20, the pivotable fenestrations 16a, 16b are positioned circumferentially at approximately 1:30 and 10:30. Such positioning may vary to enable the pivotable fenestrations 85a, 85b to generally align with the renal arteries 116 as previously described. The limb 78 may be positioned circumferentially at 9 o'clock and the fenestration 24 may be positioned circumferentially at 3 o'clock.

In FIGS. 6-13, the internal limb 22 may be initially positioned circumferentially at 3 o'clock and then rotate circumferentially around the prosthesis 26 such that the proximal end 72 of the contoured internal limb 22 is positioned circumferentially at 6 o'clock as shown in FIG. 8. Thus, the orientation of the internal limb 22 to the clock position of 6 o'clock positions the internal limb 22 away from the fenestrations 85, 86 and the scallop 88 to minimize interference within the prosthesis 26. In FIGS. 17-21, the internal limb 22 is circumferentially positioned at 3 o'clock.

The prosthesis 26 with the contoured internal limb 22 may be inserted into an original or existing prosthesis 102 that needs repair. The contoured internal limb 22 allows a wire, catheter, dilator or other device, such as an iliac limb extension, to be inserted through the original or existing stent graft leg or limb and the contoured internal limb 22 and for cannulation of the contralateral gate of the prosthesis 26, or the side of the prosthesis 26 opposite the limb 78 of the prosthesis 26, through the existing stent graft leg or limb.

FIGS. 14-16 show an example of an existing prosthesis 102 that is a bifurcated prosthesis inside a patient's body over an aneurysm 118. Similar to the prosthesis 26, the existing prosthesis 102 may include a plurality of stents, as described previously above, or be free of stents. In FIGS. 14-16, the existing prosthesis 102 includes a plurality of stents. The existing prosthesis 102 includes a stent graft body 104 that includes a main tubular body 106 having a proximal end 108 and a distal end 110, a first limb 112 extending from the distal end 110 of the main tubular body 106, and a second limb 114 also extending from the distal end 110 of the main tubular body 106. The first limb 112 and the second limb 114 extend through the patient's iliac arteries 120. Although FIGS. 14-16 show the proximal end 108 of the main tubular body 106 of the existing prosthesis 102 positioned below the renal arteries 116, the existing prosthesis 102 may be positioned above or next to the renal arteries 116. In such an example, the existing prosthesis 102 may also include fenestrations within the stent graft body 104 to allow blood flow from the renal arteries 116.

FIG. 15 shows the prosthesis 26 inserted into the existing prosthesis 102. The pivotable fenestrations 85 of the prosthesis 26 are positioned to align with the renal arteries 116 and therefore the proximal end 77 of the tubular main body 76 of the prosthesis 26 extends beyond the proximal end 108 of the main tubular body 106 of the existing prosthesis 102. The limb 78 of the prosthesis 26 extends through the first limb 112 of the existing prosthesis 102, and the fenestration 24 and the contoured internal limb 22 are positioned over the second limb 114 of the existing prosthesis 102. FIG. 16 shows an iliac limb extension 122 that is inserted into the second limb 114 of the existing prosthesis 102 and then through the fenestration 24 and the contoured internal limb 22 of the prosthesis 26. The iliac limb extension 122 includes a tubular stent graft body. The prosthesis 26 and the iliac limb extension 122 repair the existing prosthesis 102. Although FIGS. 14-16 show the prosthesis 26 with the contoured internal limb 22 extending helically around and up the posterior side 84 of tubular main body 76, these same steps may be used to repair the existing prosthesis 102 with the prosthesis 26 with the contoured internal limb 22 extending between the anterior and posterior sides 83, 84 shown in FIGS. 17-21.

It will be appreciated by those skilled in the art that changes could be made to the embodiments described above without departing from the broad inventive concept therefore. It is understood, therefore, that this invention is not limited to the particular embodiments disclosed, but it is intended to cover modifications within the spirit and scope of the present invention as defined by the claims.

The invention claimed is:

1. A method of making a contoured internal limb, the method comprising:
   providing a tubular segment of graft material;
   laying the tubular segment of graft material flat, the tubular segment of graft material comprising a left lateral edge, a right lateral edge, a first length extending from the left lateral edge to the right lateral edge, and a second length extending from a proximal end to a distal end of the tubular segment;
   contouring a proximal portion of the contoured internal limb from the tubular segment, the proximal portion comprising a first length smaller than the first length of the tubular segment and a second length extending from the proximal end of the tubular segment and along a portion of the second length of the tubular segment;
   contouring a middle portion of the contoured internal limb from the tubular segment, the middle portion comprises two sections, the first section extending at an angle from the proximal portion to the right lateral edge of the tubular segment, and the second section extending from the first section and along the right lateral edge of the tubular segment for a length smaller than the second length of the proximal portion;

contouring a distal portion of the contoured internal limb from the tubular segment, the distal portion extending from the second section of the middle portion and tapering to the left lateral edge of the tubular segment to the distal end of the tubular segment;

closing a right lateral edge of the proximal portion and a right lateral edge of the first section of the middle portion; and removing the proximal, middle and distal portions of the contoured internal limb from the tubular segment and maintaining the second section of the middle portion as circumferentially continuous.

2. The method of claim 1, wherein the removing of the proximal, middle and distal portions of the contoured internal limb from the tubular segment comprises cutting along the contouring of the proximal, middle and distal portions while maintaining the proximal and middle sections closed.

3. The method of claim 1, wherein the closing of the right lateral edge of the proximal portion and the right lateral edge of the first section of the middle portion of the contoured internal limb comprises stitching.

4. The method of claim 1, wherein the method further comprises providing a ring and attaching the ring to a proximal end of the proximal portion of the contoured internal limb.

5. The method of claim 1, wherein the method comprises inserting the proximal portion of the contoured internal limb into a fenestration of a prosthesis and connecting the distal portion of the contoured internal limb to the fenestration of the prosthesis.

6. The method of claim 5, wherein the fenestration of the prosthesis comprises a diamond fenestration and the tapering of the distal portion of the contoured internal limb conforms to the diamond fenestration.

7. The method of claim 5, wherein the fenestration of the prosthesis comprises an oval shaped fenestration and the tapering of the distal portion of the contoured internal limb conforms to the oval shaped fenestration.

8. The method of claim 5, wherein the method further comprises connecting the proximal portion of the contoured internal limb to an interior of the prosthesis.

9. The method of claim 5, wherein the connecting of the distal portion of the contoured internal limb to the fenestration of the prosthesis comprises stitching.

10. A method of making a contoured internal limb for insertion into a fenestration of a prosthesis, the method comprising:

providing a flattened tubular segment of graft material comprising a left lateral edge, a right lateral edge, a width extending from the left lateral edge to the right lateral edge, and a length extending from a proximal end to a distal end of the tubular segment;

contouring a proximal portion of the contoured internal limb from the tubular segment, the proximal portion comprising a width smaller than the width of the tubular segment and a length extending from the proximal end of the tubular segment and along a portion of the length of the tubular segment;

contouring a middle portion of the contoured internal limb from the tubular segment, the middle portion extending from the proximal portion to the right lateral edge of the tubular segment and along the right lateral edge of the tubular segment for a length smaller than the length of the proximal portion;

contouring a distal portion of the contoured internal limb from the tubular segment, the distal portion extending from the middle portion and tapering to the left lateral edge of the tubular segment to the distal end of the tubular segment to conform to the fenestration of the prosthesis;

closing a right lateral edge of the proximal portion and the section of the middle portion extending from the proximal portion to the right lateral edge of the tubular segment;

removing the proximal, middle and distal portions of the contoured internal limb from the tubular segment and maintaining the section of the middle portion that extends along the right lateral edge of the tubular segment as circumferentially continuous;

inserting the proximal portion of the contoured internal limb into the fenestration of the prosthesis; and connecting the distal portion of the contoured internal limb to the fenestration of the prosthesis.

11. The method of claim 10, wherein the method further comprises connecting the right lateral edge of the proximal portion of the contoured internal limb to an interior of the prosthesis.

12. The method of claim 10, wherein the connecting of the distal portion of the contoured internal limb to the diamond fenestration of the prosthesis comprises stitching.

13. The method of claim 10, wherein the removing of the proximal, middle and distal portions of the contoured internal limb from the tubular segment comprises cutting along the contouring of the proximal, middle and distal portions while maintaining the proximal and middle sections closed.

14. The method of claim 10, wherein the closing of the right lateral edge of the proximal portion and the open section of the middle portion of the contoured internal limb comprises stitching.

15. The method of claim 10, wherein the method further comprises providing a ring and attaching the ring to a proximal end of the proximal portion of the contoured internal limb.

16. The method of claim 10, wherein the fenestration of the prosthesis comprises a diamond shaped fenestration and the tapering of the distal portion of the contoured internal limb conforms to the diamond fenestration.

\* \* \* \* \*